United States Patent
Franklin et al.

(10) Patent No.: US 6,287,544 B1
(45) Date of Patent: *Sep. 11, 2001

(54) ANTIPERSPIRANT COMPOSITIONS

(75) Inventors: Kevin Ronald Franklin; Adam Jan Kowalski; Isabelle Claire Esser; Kathryn Elizabeth Rowe, all of Bebington (GB)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/547,604

(22) Filed: Apr. 12, 2000

(30) Foreign Application Priority Data

Apr. 12, 1999 (GB) .................................... 9908218

(51) Int. Cl.$^7$ ............... A61K 7/32; A61K 7/34; A61K 7/36; A61K 7/00
(52) U.S. Cl. .................. 424/65; 424/66; 424/68; 424/400; 424/401
(58) Field of Search ................. 424/65, 66, 68, 424/400, 401

(56) References Cited

U.S. PATENT DOCUMENTS

| | | |
|---|---|---|
| 3,969,087 | 7/1976 | Saito et al. . |
| 4,673,570 | 6/1987 | Soldati . |
| 4,948,578 | 8/1990 | Burger et al. . |
| 5,455,026 | 10/1995 | Bahr et al. . |
| 5,500,209 | 3/1996 | Ross et al. . |
| 5,587,153 | 12/1996 | Angelone, Jr. et al. . |
| 5,783,657 | 7/1998 | Pavlin et al. . |

FOREIGN PATENT DOCUMENTS

| | | |
|---|---|---|
| 1485694 | 9/1977 | (GB) . |
| 94/24997 | 11/1994 | (WO) . |
| 98/27954 | 7/1998 | (WO) . |
| 99/06473 | 2/1999 | (WO) . |

OTHER PUBLICATIONS

International Search Report Application No. PCT/GB 00/01244 mailed Oct. 24, 2000.
Takada et al. "Discotic Columnar Liquid Crystals in Oligosaccharide Deriatives III Anomeric Effects on the Termo–Mesomorphic Properties of Cellobiose OcraAlkanoates" Liquids Crystals, GB, Taylor and Francis, Ltd., London, vol. 19 No.4, pp. 441–448 –XP 000545756.
Nobohiro et al. "Gelation of Fully Acylated Cellobiose in Alkane Solution" Bull. Chem. Soc. Japan, vol. 68, 1995, pp. 3423–3428 –XP 002127501.

*Primary Examiner*—Shelley A. Dodson
(74) *Attorney, Agent, or Firm*—Matthew Boxer

(57) ABSTRACT

A cosmetic composition preferably an antiperspirant composition, in solid or soft-solid form has a continuous phase which contains a water-immiscible liquid carrier and also contains a structurant which is partially or fully esterified cellobiose of the formula

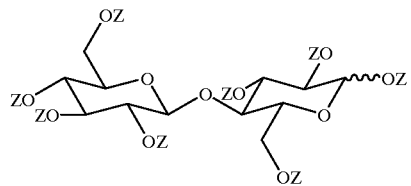

wherein each Z is independently hydrogen or an acyl group of the formula

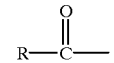

where R denotes a hydrocarbyl group containing from 4 to 22 carbon atoms. Not more than half of the Z groups are hydrogen.

25 Claims, No Drawings

ANTIPERSPIRANT COMPOSITIONS

The following U.S. patent applications are co-pending with, and commonly assigned with, the present application:

U.S. Ser. No. 09/548,309 to Franklin et al., filed Apr. 12, 2000;

U.S. Ser. No. 09/548,310 to Franklin et al., filed Apr. 12, 2000;

U.S. Ser. No. 09/547,804 to Franklin et al., filed Apr. 11, 2000;

U.S. Ser. No. 09/547,625 to Franklin et al., filed Apr. 12, 2000;

U.S. Ser. No. 09/547,445 to Esser et al., filed Apr. 12, 2000; and

U.S. Ser. No. 09/592,130 to Franklin et al., filed Jun. 12, 2000.

FIELD OF THE INVENTION

The present invention relates to antiperspirant compositions with sufficient rigidity to sustain their own shape. The usual form of such compositions is a stick.

BACKGROUND OF THE INVENTION

Topically applied antiperspirant compositions are in widespread use throughout much of the world, in order to enable their users to avoid or minimise wet patches on their skin, especially in axillary regions. Antiperspirant formulations have been applied using a range of different applicators depending on the individual preferences of consumers, including aerosols, roll-ons, pump sprays, sticks and so-called mushroom applicators which are used to apply cream formulations. In some parts of the world, sticks are especially popular. The term stick traditionally indicates a bar of material with a solid appearance which was usually housed within a dispensing container and which retains its structural integrity and shape whilst being applied. When a portion of the stick is drawn across the skin surface a film of the stick composition is transferred to the skin surface. Although the stick has the appearance of a solid article capable of retaining its own shape for a period of time, the material usually has a structured liquid phase so that a film of the composition is readily transferred from the stick to another surface upon contact. More recently, the term "stick" has been loosely applied to soft solids, which have a solid form during storage, but which flow under mild pressure or shear, so that in use they can be extruded through an aperture or apertures onto a dispensing surface.

Antiperspirant sticks have been made with a variety of different types of composition. Suspension sticks go contain a particulate antiperspirant active suspended in a structured carrier material which may well be anhydrous. Solution sticks have the antiperspirant active dissolved in a structured carrier which is polar and may be aqueous or may be based on a non-aqueous polar solvent such as ethanol. A third form of stick is an emulsion of two phases where the continuous phase is structured so that the composition is able to sustain its own shape, the antiperspirant active being dissolved in the more polar of the two phases present. In some emulsion sticks the antiperspirant active is dissolved in an aqueous disperse phase so that the composition can be classified as a water-in-oil emulsion. The classification into suspension, emulsion and solution types can be applied to both firm and soft solid compositions.

Although a number of documents have disclosed emulsion sticks, the marketplace has avoided them. Antiperspirant stick products currently on the market are either suspension sticks in which the antiperspirant active is dispersed in particulate form or are solution sticks in which the antiperspirant active is dissolved in a structured single phase which tends to feel tacky or draggy when applied to the skin.

There is substantial literature on the structuring or thickening of antiperspirant compositions which is frequently accomplished using some form of thickening agent as part of the composition.

Structuring a stick by the incorporation of a thickening polymer has been disclosed in a number of documents including U.S. Pat. No. 5,500,209, U.S. Pat. No. 5,783,657 and WO 99/06473.

A class of polymers which has been used in this way is the polyamides. Compositions in this way tend to have poor sensory properties experienced by the user, notably a sticky or rubbery feel as they are applied.

It has been common practice for sticks to be structured by incorporating fatty alcohol and/or wax into the composition. Sticks which are structured with fatty alcohol or wax tend to leave visible white deposits on application to human skin. These deposits can also transfer onto clothing when it comes into contact with the skin and the wearer can, for example, find white marks on the armhole of a sleeveless garment.

There have been some disclosures of antiperspirant stick compositions where structuring to a shape-sustaining stick has been accomplished without using a fatty alcohol or wax. Amongst these disclosures there has sometimes been recognition that white deposits are avoided.

Antiperspirant stick compositions are known which do not contain a structuring agent and which are translucent or transparent. U.S. Pat. No. 4,948,578 discloses transparent antiperspirant sticks formed as emulsions where the aqueous phase contains a large proportion of nonionic surfactant as well as water and dissolved antiperspirant active.

Compositions with high viscosity but without gelling or structuring agent are also disclosed in U.S. Pat. No. 4,673,570 and U.S. Pat. No. 5,587,153. These compositions are believed to take the form of creams or soft gels which are extruded from a suitable package by the user.

In some compositions structuring has been achieved by the incorporation of a structurant (also referred to as a gellant or gelling agent) which causes the liquid to gel upon cooling from an elevated temperature. Gel formation takes place as an exothermic event within a temperature range referred to as the gel point; upon reheating, melting of the gel takes place as an endothermic event within a temperature range. Such gels can be disrupted by shearing and do not recover their structure for a long time, if at all unless remelted, although a small partial recovery may be observed.

U.S. Pat. No. 5,455,026 (Bahr) discloses and exemplifies gels of silicone oil containing 12-hydroxystearic acid—frequently in rather small amounts—together with a particulate antiperspirant active. A further possibility which is mentioned but never exemplified is that the antiperspirant active may be present in solution in an organic solvent. Ethanol and propylene glycol are mentioned as possibilities. This document states that clear gels may be obtained by matching the refractive index of the antiperspirant to that of the silicone oil.

Fatty acyl amino acid amides, 12-hydroxy stearic acid and dibenzylidene sorbitol are all examples of compounds which are able to gel and hence structure at least some hydrophobic, water-immiscible organic liquids, although dibenzylidene sorbitol will not structure an organic liquid if an acidic aqueous phase is present, because it will be hydrolysed rapidly. We now believe that they function by forming a network of fibres, which appear to be branched or interconnected, and which extend throughout the liquid and thereby give it rigidity. When the gel melts these fibres dissolve in the liquid.

Some ingredient materials which are used in sticks have accompanying disadvantages which are a complicating factor in the formulation of compositions. If a polar organic solvent is volatile, like ethanol, the stick gives a cooling sensation when applied. Some cooling may be desired but too much may prove unacceptable to consumers. Polar but less volatile solvents such as water-immiscible diols tend to make a stick feel tacky when touched and hence give a sensation of stickiness and drag when applied to skin.

SUMMARY OF THE INVENTION

We have now discovered that it is possible to formulate antiperspirant compositions which are structured emulsions where the continuous phase is hydrophobic and the disperse phase is a solution of the antiperspirant active in an aqueous solvent, while moreover, the composition has a transparent or translucent appearance.

With suitable choice of materials and proportions it is possible to achieve other advantages, notably satisfactory sensory perception when applied to the skin by the user firmness of the composition, avoidance of highly visible opaque deposits on skin or clothing.

According to a first aspect of this invention there is provided an antiperspirant composition which is a structured emulsion comprising i) a continuous phase containing water-immiscible liquid carrier and a structurant present therein, ii) a disperse phase which is a solution of antiperspirant active in water, optionally including water-soluble solvent, where the composition is sufficiently translucent or transparent that it has at least 1% light transmittance at 580 nm through a 1 cm thickness of the composition at 22° C.

The structurant serves to gel the continuous phase giving it an increased viscosity or even rigidity. When used in a sufficient amount, which is likely to be less than 15% or 20% of the total composition, it is able to structure the composition with sufficient rigidity to sustain its own shape, at least for a limited time.

A preferred structurant forms a network of fibres or strands extending throughout the water-immiscible continuous phase. These are believed to be branched or interconnected. Upon heating the gel to the gel melting temperature, the strands of structurant dissolve in the liquid phase.

Formulation of an emulsion composition to possess transparency or translucency in accordance with this invention can be achieved by observing two criteria. The first criterion is that the disperse phase and the continuous phase (consisting of the water-immiscible carrier liquid and the structurant contained within that liquid) should be formulated so that their refractive indices match. The refractive index of the continuous phase will be close to the refractive index of the water-immiscible carrier liquid in it. In order to achieve good light transmission through a composition, the refractive index of the water-immiscible continuous phase and the refractive index of the disperse phase should match within 0.003 units preferably 0.002 units.

The second criterion is that the matched refractive indices of these two phases should be an approximate match to the refractive index of the structurant. The closeness of match required will depend on the structurant which is used. The refractive index of a structurant can be determined by making trial compositions as explained in more detail below. Such investigation will also show how closely the refractive index of the liquid must be matched to the structurant. It is likely that the matched refractive indices of the liquid phases will be not over 0.07 units below and not over 0.04 units above the refractive index of the structurant.

Preferred within this invention are compositions which have sufficient rigidity that they can be regarded as firm solids. The hardness of such compositions can be measured with a penetrometer, in a manner which will be described in greater detail below.

In order to promote good sensory properties at the time of use it is preferred to include silicone oil in the water-immiscible carrier liquid. The amount of silicone oil may be at least 10% by weight of the composition and/or at least 40% by weight of the water-immiscible carrier liquid.

Ethanol gives a cooling effect on application to skin, because it is very volatile. It is preferred that the content of ethanol or any monohydric alcohol with a vapour pressure above 1.3 kPa (10 mm Hg) is not over 15% better not over 8% by weight of the composition.

Fatty alcohols which are solid at room temperature, such as stearyl alcohol, lead to deposits with an opaque white appearance and are preferably kept to low concentration or excluded.

A composition of this invention will generally be marketed in a container by means of which it can be applied at time of use. This container may be of conventional type.

A second aspect of the invention therefore provides an antiperspirant product comprising a dispensing container having at least one aperture for delivery of the contents of the container, means for urging the contents of the container to the said aperture or apertures, and a composition of the first aspect of the invention in the container. Preferred is that a composition of this invention is sufficiently rigid to be accommodated as a stick product in a dispensing container having an open end at which an end portion of the stick of composition is exposed for use.

The compositions of this invention can be produced by processes in which an emulsion is produced at an elevated temperature and allowed to cool to permit gel-formation in the continuous phase.

Thus, according to a third aspect of the present invention there is provided a process for the production of an antiperspirant composition according to the first aspect of this invention comprising, not necessarily in any order, the steps of incorporating a structurant into a water-immiscible liquid carrier mixing the liquid carrier with a disperse liquid phase which is a solution of an antiperspirant active in water, optionally mixed with a water-soluble solvent, heating the liquid carrier or a mixture containing it to an elevated temperature at which the structurant is soluble in the water-immiscible liquid carrier, followed by introducing the mixture into a would which preferably is a dispensing container, and then cooling or permitting the mixture to cool to a temperature at which it is thickened or solidified.

According to a fourth aspect of the present invention, there is provided a method for preventing or reducing perspiration on human skin comprising topically applying to the skin a composition according to the first aspect of this invention comprising an antiperspirant active, a water-immiscible liquid carrier and a structurant therefor.

DETAILED DESCRIPTION AND PREFERRED EMBODIMENTS

As indicated above, the composition contains an aqueous solution of antiperspirant active emulsified in a carrier oil containing a structuring agent.

Materials which may be used to form these different parts of the composition will be discussed in turn, together with possibilities and preferences.

Structurant

A number of organic compounds are known to possess the ability to gel hydrophobic organic liquids such as water-immiscible hydrocarbon and/or silicone oils by formation of a network of fibres or strands which extends throughout the liquid, thereby gelling the liquid. Such materials are generally non-polymeric, being monomers or dimers with molecular weight below 10,000 rather than polymers with more than 8 repeat units or with molecular weight above 10,000.

Materials with this property have been reviewed by Terech and Weiss in "Low Molecular Mass Gelators of Organic Liquids and the Properties of their Gels" Chem. Rev 97, 3133–3159 [1997] and by Terech in Chapter 8, "Low-molecular Weight Organogelators" of the book "Specialist Surfactants" edited by I D Robb, Blackie Academic Professional, 1997.

It is characteristic of such structurants that
- they are able to gel the organic liquid in the absence of any disperse phase the structured liquids are obtainable by cooling from an elevated temperature at which the structurant is in solution in the liquid—this solution being mobile and pourable
- the structured liquid becomes more mobile if subjected to shear or stress
- the structure does not spontaneously recover within 24 hours if the sheared liquid is left to stand at room temperature, even though a small partial recovery may be observed
- the structure can be recovered by reheating to a temperature at which the structurant is in solution in the liquid and allowing it to cool back to room temperature.

It appears that such structurants operate by interactions which are permanent unless disrupted by shear or heating. Such structurants operate by forming a network of strands or fibres extending throughout the gelled liquid. In some cases these fibres can be observed by electron microscopy, although in other cases the observation of the fibres which are believed to be present is prevented by practical difficulties in preparing a suitable specimen. When observed, the fibres in a gel are generally thin (diameter less than 0.5 $\mu$, often less than 0.2 $\mu$) and appear to have numerous branches or interconnections.

If these fibres are crystalline, they may or may not be the same polymorph as macroscopic crystals obtained by conventional crystallization from a solvent.

One material which is well known to form gels is 12-hydroxy stearic acid which is discussed in Terech et al "Organogels and Aerogels of Racemic and Chiral 12-hydroxy octadecanoic Acid", Langmuir Vol 10, 3406–3418, 1994. U.S. Pat. No. 5,750,096 is one of several documents which teaches that gelation can be brought about using esters or amides of 12-hydroxy stearic acid. The alcohol used to form such an ester or the amine used to form such an amide may contain an aliphatic, cycloaliphatic or aromatic group with up to 22 carbons therein. If the group is aliphatic it preferably contains at least three carbon atoms. A cycloaliphatic group preferably contains at least five carbon atoms and may be a fixed ring system such as adamantyl.

N-acyl amino acid amides and esters are also known to structure liquids. We have established that they do so by forming fibrous networks. They are described in U.S. Pat. No. 3,969,087. N-Lauroyl-L-glutamic acid di-n-butylamide is commercially available from Ajinomoto under their designation GP-1.

Further materials which have been disclosed as gelling agents are the amide derivatives of di and tribasic carboxylic acids set forth in WO 98/27954 notably alkyl N,N'dialkyl succinamides.

It is desirable that the structurant material(s) should not include carboxylic acid groups which can react with common antiperspirant acid salts in solution and form a precipitate of an insoluble aluminium or zirconium salt.

It is also desirable that the structurant material(s) should not include any functional groups which are vulnerable to hydrolysis under acidic aqueous conditions.

For these reasons the N-acylamino acid amides, the amides of 12-hydroxy stearic acid and the above-mentioned succinamides are of interest.

A novel structurant which is the subject of a co-pending application and which may be used in this invention is an ester of cellobiose and a fatty acid, preferably of 6 to 13 carbon atoms especially 8 to 11 carbon atoms. Preferably the cellobiose is fully esterified, or nearly so, and is in the α-anomeric form.

The structure of such a compound in its α-anomeric form is:

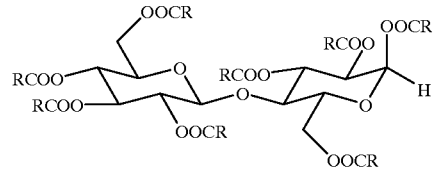

where R is an alkyl or alkenyl chain of 5 to 12 carbon atoms so that the acyl group contains 6 to 13 carbon atoms. Particularly preferred acyl groups incorporate a linear alkyl chain of 7 to 10 carbon atoms and are thus octanoyl, nonanoyl, decanoyl or undecanoyl.

The acyl groups may have a mixture of chain lengths but it is preferred that they are similar in size and structure. Thus it is preferred that all of the acyl groups are aliphatic and at least 90% of the acyl groups have a chain length within a range such that the shorter and longer chain lengths in the range differ by no more than two carbon atoms, i.e. length in a range from m−1 to m+1 carbon atoms where the mean acyl chain length m has a value in a range from 7 to 10 or 11. Commercially available feedstocks for these acyl groups are likely to include a small percentage of acyl groups which differ from the majority and may have a branched rather than linear chain. Thus it is likely that more than 90% but less than 100% of the acyl groups will meet the desired criterion of chain lengths in a range from m−1 to m+1 carbon atoms.

Linear aliphatic acyl groups may be obtained from natural sources, in which case the number of carbon atoms in the acyl group is likely to be an even number or may be derived synthetically from petroleum as the raw material in which case both odd an even numbered chain lengths are available.

Synthetic methods for the esterification of saccharides are well known. The esterification of cellobiose has been reported by Takada et al in *Liquid Crystals*, (1995) Volume 19, pages 441–448. This article gives a procedure for the production of the alpha anomers of cellobiose octa-alkanoates by esterification of β-cellobiose using an alkanoic acid together with trifluoracetic anhydride.

The amount of structurant in an emulsion composition of this invention is likely to be from 0.5% to 25% or 30% by weight of the continuous phase, more likely from 1% to 16% or 20% of this phase. As a percentage of the whole composition the amount is likely to be from 0.5 or 1% up to 15% or 20%, probably from 1 to 12%.

If two structurants are used together, then the above percentages are likely to apply to the total amount of structurant.

Carrier Liquid

The water-immiscible carrier liquid in the continuous phase comprises one or a mixture of materials which are relatively hydrophobic so as to be immiscible in water. Some hydrophilic liquid may be included in the carrier, provided the overall carrier liquid mixture is immiscible with water. It will generally be desired that this carrier is liquid (in the absence of structurant) at temperatures of 15° C. and above. It may have some volatility but its vapour pressure will generally be less than 4 kPa (30 mm Hg) at 25° C. so that the material can be referred to as an oil or mixture of oils. More specifically, it is desirable that at least 80% by weight of the hydrophobic carrier liquid should consist of materials with a vapour pressure not over this value of 4 kPa at 25° C.

It is preferred that the hydrophobic carrier material includes a volatile liquid silicone, i.e. liquid polyorganosiloxane. To class as "volatile" such material should have a measurable vapour pressure at 20 or 25° C. Typically the vapour pressure of a volatile silicone lies in a range from 1 or 10 Pa up to 2 kPa at 25° C.

It is desirable to include volatile silicone because it gives a "drier" feel to the applied film after the composition is applied to skin.

Volatile polyorganosiloxanes can be linear or cyclic or mixtures thereof. Preferred cyclic siloxanes include polydimethsiloxanes and particularly those containing from 3 to 9 silicon atoms and preferably not more than 7 silicon atoms and most preferably from 4 to 6 silicon atoms, otherwise often referred to as cyclomethicones. Preferred linear siloxanes include polydimethylsiloxanes containing from 3 to 9 silicon atoms. The volatile siloxanes normally by themselves exhibit viscosities of below $10^{-5}$ m$^2$/sec (10 centistokes), and particularly above $10^{-7}$ m$^2$/sec (0.1 centistokes), the linear siloxanes normally exhibiting a viscosity of below $5 \times 10^{-6}$ m$^2$/sec (5 centistokes). The volatile silicones can also comprise branched linear or cyclic siloxanes such as the aforementioned linear or cyclic siloxanes substituted by one or more pendant —O—Si(CH$_3$)$_3$ groups. Examples of commercially available silicone oils include oils having grade designations 344, 345, 244, 245 and 246 from Dow Corning Corporation; Silicone 7207 and Silicone 7158 from Union Carbide Corporation; and SF1202 from General Electric.

The hydrophobic carrier employed in compositions herein can alternatively or additionally comprise non-volatile silicone oils, which include polyalkyl siloxanes, polyalkylaryl siloxanes and polyethersiloxane copolymers. These can suitably be selected from dimethicone and dimethicone copolyols. Commercially available non-volatile silicone oils include Dow Corning 556 and Dow Corning 200 series.

The water-immiscible liquid carrier may contain from 0 to 100% by weight of one or more liquid silicones. Preferably, there is sufficient liquid silicone to provide at least 10%, better at least 15%, by weight of the whole composition. If silicone oil is used, volatile silicone preferably lies in a range from 20% possibly from 30 or 40% up to 100% of the weight of the water-immiscible carrier liquid. In many instances, when a non-volatile silicone oil is present, its weight ratio to volatile silicone oil is chosen in the range of from 1:3 to 1:40.

Silicon-free hydrophobic liquids can be used instead of, or more preferably in addition to liquid silicones. Silicon-free hydrophobic organic liquids which can be incorporated include liquid aliphatic hydrocarbons such as mineral oils or hydrogenated polyisobutene, often selected to exhibit a low viscosity. Further examples of liquid hydrocarbons are polydecene and paraffins and isoparaffins of at least 10 carbon atoms.

Other hydrophobic carriers are liquid aliphatic or aromatic esters. Suitable aliphatic esters contain at least one long chain alkyl group, such as esters derived from $C_1$ to $C_{20}$ alkanols esterified with a $C_8$ to $C_{22}$ alkanoic acid or $C_6$ to $C_{10}$ alkanedioic acid. The alkanol and acid moieties or mixtures thereof are preferably selected such that they each have a melting point of below 20° C. These esters include isopropyl myristate, lauryl myristate, isopropyl palmitate, diisopropyl sebacate and diisopropyl adipate.

Suitable liquid aromatic esters, preferably having a melting point of below 20° C., include fatty alkyl benzoates. Examples of such esters include suitable $C_8$ to $C_{18}$ alkyl benzoates or mixtures thereof.

Further instances of suitable hydrophobic carriers comprise liquid aliphatic ethers derived from at least one fatty alcohol, such as myristyl ether derivatives e.g. PPG-3 myristyl ether or lower alkyl ethers of polyglycols such as PPG-14 butyl ether.

Aliphatic alcohols which are solid at 20° C., such as stearyl alcohol are preferably absent or present in low concentration such as less than 5% by weight of the whole composition since these lead to visible white deposits when a composition is used.

However, aliphatic alcohols which are liquid at 20° C. may be employed. These include branched chain alcohols of at least 10 carbon atoms such as isostearyl alcohol and octyl dodecanol.

Very polar materials are preferably excluded or present in only small quantity in the water-immiscible carrier liquid. Preferably therefore, this liquid or mixture of liquids contains not more than 10% of its own weight, better not more than 5%, of any constituent which is a water-miscible compound.

Silicon-free liquids can constitute from 0–100% of the water-immiscible liquid carrier, but it is preferred that silicone oil is present and that the amount of silicon-free constituents preferably constitutes up to 50 or 60% and in many instances from 10 or 15% up to 50 or 60% by weight of the carrier liquid.

If any oxygen-containing silicon-free organic liquids are included in the hydrophobic carrier liquid, the amount of them is likely to be not over 70% by weight of the carrier liquid. Smaller amounts, ranging up to 20, 30 or 35% by weight are likely.

The carrier liquid must be compatible with the structurant. If the structurant is too soluble or conversely is very insoluble in the carrier liquid it may fail to form a gel and the carrier liquid should be modified to alter its polarity.

Disperse Phase Solvent

The disperse phase is a solution of an antiperspirant active ingredient in a solvent which is more polar than the carrier liquid of the disperse phase. This disperse phase comprises water as solvent and can comprise one or more water-soluble or water-miscible liquids in addition to water.

One class of water soluble or water-miscible liquids comprises short chain monohydric alcohols, e.g. $C_1$ to $C_4$ and especially ethanol or isopropanol, which can impart a deodorising capability to the formulation. A further class of hydrophilic liquids comprises diols or polyols preferably having a melting point of below 40° C., or which are water miscible. Examples of water-soluble or water-miscible liquids with at least one free hydroxy group include ethylene glycol, 1,2-propylene glycol, 1,3-butylene glycol, hexylene glycol, diethylene glycol, dipropylene glycol, 2-ethoxyethanol, diethylene glycol monomethylether, triethyleneglycol monomethylether and sorbitol. Especially preferred are propylene glycol and glycerol.

The disperse phase is likely to constitute from 5 to 80 or 85% of the weight of the composition preferably from 5 to 50 or 65% more preferably from 25 or 35% up to 50 or 65%, while the continuous phase with the structurant therein provides the balance from 15 or 35% up to 95% of the weight of the composition. Compositions with a high proportion of disperse phase i.e. from 65 to 85% disperse phase may be advantageous because the large proportion of disperse phase can make a contribution to hardness. The proportion of water in an emulsion according to the present invention is often selected in the range of up to 60%, and particularly from 10% up to 40% or 50% of the whole formulation.

A composition of this invention will generally include one or more emulsifying surfactants which may be anionic, cationic, zwitterionic and/or nonionic surfactants. The proportion of emulsifier in the composition is often selected in the range up to 10% by weight and in many instances from 0.1 or 0.25 up to 5% by weight of the composition. Most preferred is an amount from 0.1 or 0.25 up to 3% by weight. Nonionic emulsifiers are frequently classified by HLB value. It is desirable to use an emulsifier or a mixture of emulsifiers with an overall HLB value in a range from 2 to 10 preferably from 3 to 8.

It may be convenient to use a combination of two or more emulsifiers which have different HLB values above and below the desired value. By employing the two emulsifiers together in appropriate ratio, it is readily feasible to attain a weighted average HLB value that promotes the formation of an emulsion.

Many suitable emulsifiers of high HLB are nonionic ester or ether emulsifiers comprising a polyoxyalkylene moiety, especially a polyoxyethylene moiety, often containing from about 2 to 80, and especially 5 to 60 oxyethylene units, and/or contain a polyhydroxy compound such as glycerol or sorbitol or other alditol as hydrophilic moiety. The hydrophilic moiety can contain polyoxypropylene. The emulsifiers additionally contain a hydrophobic alkyl, alkenyl or aralkyl moiety, normally containing from about 8 to 50 carbons and particularly from 10 to 30 carbons. The hydrophobic moiety can be either linear or branched and is often saturated, though it can be unsaturated, and is optionally fluorinated. The hydrophobic moiety can comprise a mixture of chain lengths, for example those deriving from tallow, lard, palm oil, sunflower seed oil or soya bean oil. Such nonionic surfactants can also be derived from a polyhydroxy compound such as glycerol or sorbitol or other alditols. Examples of emulsifiers include ceteareth-10 to -25, ceteth-10-25, steareth-10-25 (i.e. C16 to C18 alcohols ethoxylated with 10 to 25 ethylene oxide residues) and PEG-15–25 stearate or distearate. Other suitable examples include $C_{10}$–$C_{20}$ fatty acid mono, di or tri-glycerides. Further examples include $C_{18}$–$C_{22}$ fatty alcohol ethers of polyethylene oxides (8 to 12 EO).

Examples of emulsifiers, which typically have a low HLB value, often a value from 2 to 6 are fatty acid mono or possibly diesters of polyhydric alcohols such as glycerol, sorbitol, erythritol or trimethylolpropane. The fatty acyl moiety is often from $C_{14}$ to $C_{22}$ and is saturated in many instances, including cetyl, stearyl, arachidyl and behenyl. Examples include monoglycerides of palmitic or stearic acid, sorbitol mono or diesters of myristic, palmitic or stearic acid, and trimethylolpropane monoesters of stearic acid.

A particularly desirable class of emulsifiers comprises dimethicone copolymers, namely polyoxyalkylene modified dimethylpolysiloxanes. The polyoxyalkylene group is often a polyoxyethylene (POE) or polyoxypropylene (POP) or a copolymer of POE and POP. The copolymers often terminate in $C_1$ to $C_{12}$ alkyl groups.

Suitable emulsifiers and co-emulsifiers are widely available under many trade names including Abil™, Arlacel™, Brij™, Cremophor, Dehydrol™, Dehymuls™, Emerest™, Lameform™, Pluronic™, Prisorine™, Quest PGPR™, Span™, Tween™, SF1228, DC3225C and Q2-5200.

Antiperspirant Actives

Antiperspirant actives, are preferably incorporated in an amount of from 0.5–60%, particularly from 5 to 30% or 40% and especially from 5 or 10% to 30 or 35% of the weight of the whole composition.

Antiperspirant actives for use herein are often selected from astringent active salts, including in particular aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates.

Aluminium halohydrates are usually defined by the general formula $Al_2(OH)_xQ_y \cdot wH_2O$ in which Q represents chlorine, bromine or iodine, x is variable from 2 to 5 and x+y=6 while $wH_2O$ represents a variable amount of hydration. Especially effective aluminium halohydrate salts, known as activated aluminium chlorohydrates, are described in EP-A-6739 (Unilever NV et al), the contents of which specification is incorporated herein by reference. Some activated salts do not retain their enhanced activity in the presence of water but are useful in substantially anhydrous formulations, i.e. formulations which do not contain a distinct aqueous phase.

Zirconium actives can usually be represented by the empirical general formula: $ZrO(OH)_{2n-nz}B_z \cdot wH_2O$ in which z is a variable in the range of from 0.9 to 2.0 so that the value 2n-nz is zero or positive, n is the valency of B, and B is selected from the group consisting of chloride, other halide, sulphamate, sulphate and mixtures thereof. Possible hydration to a variable extent is represented by wH20. Preferable is that B represents chloride and the variable z lies in the range from 1.5 to 1.87. In practice, such zirconium salts are usually not employed by themselves, but as a component of a combined aluminium and zirconium-based antiperspirant.

The above aluminium and zirconium salts may have coordinated and/or bound water in various quantities and/or may be present as polymeric species, mixtures or complexes. In particular, zirconium hydroxy salts often represent a range of salts having various amounts of the hydroxy group. Zirconium aluminium chlorohydrate may be particularly preferred.

Antiperspirant complexes based on the above-mentioned astringent aluminium and/or zirconium salts can be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine which has the formula $CH_2(NH_2)COOH$.

It is highly desirable to employ complexes of a combination of aluminium halohydrates and zirconium chlorohydrates together with amino acids such as glycine, which are disclosed in U.S. Pat. No. 3,792,068 (Luedders et al). Certain of those Al/Zr complexes are commonly called ZAG in the literature. ZAG actives generally contain aluminium, zirconium and chloride with an Al/Zr ratio in a range from 2 to 10, especially 2 to 6, an Al/Cl ratio from 2.1 to 0.9 and a variable amount of glycine. Actives of this preferred type are available from Westwood, from Summit and from Reheis.

Other actives which may be utilised include astringent titanium salts, for example those described in GB 2299506A.

The proportion of solid antiperspirant salt in a composition normally includes the weight of any water of hydration and any complexing agent that may also be present in the solid active. However, when the salt is in solution, it's weight excludes any water present.

The antiperspirant active will often provide from 3 to 60% by weight of the aqueous disperse phase, particularly from 10% or 20% up to 55% or 60% of that phase.

Optional Ingredients

Optional ingredients in compositions of this invention can include deodorants, for example at a concentration of up to about 10% w/w. Suitable deodorant actives can comprise deodorant effective concentrations of antiperspirant metal salts, deoperfumes, and/or microbicides, including particularly bactericides, such as chlorinated aromatics, including biguanide derivatives, of which materials known as Irgasan DP300™ (Triclosan), Tricloban™, and Chlorhexidine warrant specific mention. A yet another class comprises biguanide salts such as available under the trade mark Cosmosil™.

Other optional ingredients include wash-off agents, often present in an amount of up to 10% w/w to assist in the removal of the formulation from skin or clothing. Such wash-off agents are typically nonionic surfactants such as esters or ethers containing a $C_8$ to $C_{22}$ alkyl moiety and a hydrophilic moiety which can comprise a polyoxyalkylene group (POE or POP) and/or a polyol.

Another optional constituent of the formulation is a polymeric secondary structurant. Examples of such structurants which can be employed include polymeric waxes and organo polysiloxane elastomers such as reaction products of a vinyl terminated polysiloxane and a cross linking agent or alkyl or alkyl polyoxyalkylene-terminated poly (methyl substituted) or poly (phenyl substituted) siloxanes. Polymers containing both siloxane and hydrogen bonding groups, which might be used as secondary structurants, have been disclosed in WO 97/36572 and WO 99/06473. A number of polyamides have also been disclosed as structurants for hydrophobic liquids. Polyacrylamides, polyacrylates or polyalkylene oxides may be used to structure or thicken the disperse phase if it is aqueous.

The compositions herein can incorporate one or more cosmetic adjuncts conventionally contemplatable for antiperspirant solids or soft solids. Such cosmetic adjuncts can include skin feel improvers, such as talc or finely divided polyethylene, for example in an amount of up to about 10%; skin benefit agents such as allantoin or lipids, for example in an amount of up to 5%; colours; skin cooling agents other than the already mentioned alcohols, such a menthol and menthol derivatives, often in an amount of up to 2%, all of these percentages being by weight of the composition. A commonly employed adjunct is a perfume, which is normally present at a concentration of from 0 to 4% and in many formulations from 0.25 to 2% by weight of the composition.

Translucent/Transparent Compositions

A composition of this invention is formulated such that the emulsion is translucent or transparent. In order to do this the refractive indices of the water-immiscible continuous phase and the polar or aqueous disperse phase must be matched to each other and the value of refractive index at which they are matched must also approximately match the refractive index of the structurant.

The refractive index of a fibrous network of a structurant can be determined by using that structurant to gel a number of oils or oil mixtures of differing refractive index. When the resulting gel is transparent, the refractive index of the oil or oil mixture(which can be determined by conventional measurement) is a good approximation to the refractive index of the structurant. The oils or mixtures or oils should be chosen from these which are gelled well by the structurant to avoid interfering effects. When the gel is not transparent, but is translucent, it will indicate a refractive index which is not precisely matched to the refractive index of the structurant, and thus indicate an amount of mismatch which can be tolerated without loss of translucency.

Some examples of oils which may be used to make mixtures which vary in refractive index are:

volatile silicone (refractive index of about 1.40)

$C12–15$ alkyl benzoate (refractive index of about 1.48) which available as Finsolv TN and/or octylmethoxycinnamate (refractive index of about 1.54) which is available as Parsol MCX.

polyphenylsiloxane (DC70) (refractive index of about 1.53)

Using this method we have determined the refractive indices of some structurants, namely:

| | |
|---|---|
| N-lauroyl L-glutamic acid di-n-butylamide | approx 1.48 |
| 12-hydroxy stearic acid | approx 1.52 |
| α-cellobiose octa-esters with $C_8$ to $C_{12}$ fatty acids | approx 1.48 |

For the continuous phase, silicon-free water-immiscible liquid oils generally have refractive indices in a range from 1.43 to 1.49 at 22° C. and can be used alone or mixed together to give a silicon-free carrier liquid with refractive index in this range. Volatile silicone oils generally have a refractive index slightly below 1.40 at 22° C., but carrier liquid mixtures with refractive indices in the range from 1.41 to 1.46 can be obtained by mixing volatile silicone with other oils. Non-volatile silicone oils generally have refractive indices in a range from 1.45 to 1.48 at 22° C. and so can be included when desired.

The refractive index of the continuous phase will be very close to the refractive index of the carrier liquid (usually a carrier liquid mixture) which is its principal component.

For the disperse phase, a solution of an antiperspirant active salt in water alone will generally display a refractive index below 1.425. The refractive index can be raised by incorporating a diol or polyol into the aqueous solution. It is believed to be novel to match the refractive index of a polar disperse phase to that of a structurant network within a continuous phase. Moreover, it can be achieved without using so much diol or polyol as will make the composition excessively sticky.

For the regular production of compositions with optimum transparency it may prove desirable to monitor the refractive indices of the raw materials to detect any batch to batch variation. If necessary the composition of a liquid phase can be adjusted by variations in the quantity of a constituent material.

Mechanical Properties and Product Packages

The compositions of this invention are structured liquids and may be firm or soft in appearance. Even a soft solid has an ability to sustain its own shape, for instance if it is removed from a mould without being subjected to shear it will retain its shape for at least 30 seconds, usually longer.

A composition of this invention will usually be marketed as a product comprising a container with a quantity of the composition therein, where the container has at least one aperture for the delivery of composition, and means for urging the composition in the container towards the delivery aperture. Conventional containers take the form of a barrel of oval cross section with the delivery apertures at one end of the barrel.

A composition of this invention is preferably sufficiently rigid that it is not apparently deformable by hand pressure, even though a surface layer will transfer as a film to skin, and is suitable for use as a stick product in which a quantity of the composition in the form of a stick is accommodated within a container barrel having an open end at which an end portion of the stick of composition is exposed for use. The opposite end of the barrel is closed.

Generally the container will include a cap for its open end and a component part which is sometimes referred to as an elevator or piston fitting within the barrel and capable of relative axial movement along it. The stick of composition is accommodated in the barrel between the piston and the open end of the barrel. The piston is used to urge the stick of composition along the barrel. The piston and stick of composition may be moved axially along the barrel by manual pressure on the underside of the piston using a finger or rod inserted within the barrel. Another possibility is that a rod attached to the piston projects through a slot or slots in the barrel and is used to move the piston and stick. Preferably the container also includes a transport mechanism for moving the piston comprising a threaded rod which extends axially into the stick through a correspondingly threaded aperture in the piston, and means mounted on the barrel for rotating the rod. Conveniently the rod is rotated by means of a handwheel mounted on the barrel at its closed end, i.e. the opposite end to the delivery opening.

If a composition of this invention is softer, but still capable of sustaining its own shape it will be more suited for dispensing from a barrel with a closure instead of an open end, where the closure has one or more apertures through which composition from the barrel can be extruded. The number and design of such apertures is at the discretion of the designer of the package.

The component parts of such containers are often made from thermoplastic materials, for example polypropylene or polyethylene. Descriptions of suitable containers, some of which include further features, are found in U.S. Pat. Nos. 4,865,231, 5,000,356 and 5,573,341.

Measurement of Properties i) Penetrometer

The hardness and rigidity of a composition which is a firm solid can be determined by penetrometry. If the composition is a softer solid, this will be observed as a substantial lack of any resistance to the penetrometer probe.

A suitable procedure is to utilises a lab plant PNT penetrometer equipped with a Seta wax needle (weight 2.5 grams) which has a cone angle at the point of the needle specified to be 90°10'±15'. A sample of the composition with a flat upper surface is used. The needle is lowered onto the surface of the composition and then a penetration hardness measurement is conducted by allowing the needle with its holder to drop under a total weight, (i.e. the combined weight of needle and holder) of 50 grams for a period of five seconds after which the depth of penetration is noted.

Desirably the test is carried out at a number of points on each sample and the results are averaged. Utilising a test of this nature, an appropriate hardness for use in an open-ended dispensing container is a penetration of less than 30 mm in this test, for example in a range from 2 to 30 mm. Preferably the penetration is in a range from 5 mm to 20 mm.

In a specific protocol for this test measurements on a stick were performed in the stick barrel. The stick was wound up to project from the open end of the barrel, and then cut off to leave a flat, uniform surface. The needle was carefully lowered to the stick surface, and then a penetration hardness measurement was conducted. This process was carried out at six different points on the stick surface. The hardness reading quoted is the average value of the 6 measurements.

ii) Texture analyser

The hardness of a softer solid can be measured by using a texture analyser. This test apparatus can move a blunt probe into or out from a sample at a controlled speed and at the same time measure the applied force. The parameter which is determined as hardness is a function of the peak force and the projected area of indentation.

A specific test protocol used a Stable Micro systems TA.XT2i Texture Analyser. A metal sphere, of diameter 9.5 mm, was attached to the underside of the *Texture Analyser's* 5 kg load cell such that it could be used for indenting a sample placed beneath it on the base plate of the instrument. After positioning the sample, the sphere position was adjusted until it was just above the sample surface. Texture Expert Exceed software was used to generate the subsequent motion profile used in the test method. This profile initially indented the sphere into the sample at an indentation speed of 0.05 mm/s until a a designated force was reached, which was chosen such that the distance of penetration into the sample was less than the radius of the sphere. At this load the direction of motion of the sphere was immediately reversed to withdraw the sphere from the sample at the same speed of 0.05 mm/s. During the course of the test, the data acquired were time(s), distance (mm) and force (N) and the data acquisition rate was 25 Hz.

Suitable samples for measurement were either contained in stick barrels, which had a screw mechanism, or in 15 ml glass jars. For the barrel samples, the stick was wound up until it protruded above the edges of the barrel and then a knife was used to skim the top of the barrel in such a way as to leave a flat uniform surface. The stick was then pushed back into the barrel as far as possible to minimise any mechanical interference resulting from the compliance of the screw mechanism in the pack. Two indents were generally made either side of the screw. The samples in the 15 ml jars needed no surface preparation but only had enough surface area for a single indentation test to be performed.

The data associated with each test were manipulated using standard spreadsheet software and used to calculate the hardness, H, using the following equation:

$$H[N/mm^2] = \frac{F_{\max}[N]}{A_p[mm^2]}$$

where $F_{max}$ is the peak load and $A_p$ is the projected area of the indentation remaining on unloading. This area can be calculated geometrically from the plastic indentation depth. This is slightly less than the total penetration depth measured under load because of elastic deformation of the sample. The plastic indentation depth is calculated from a graph of the unloading-force-versus-total-penetration-depth. The initial slope of this unloading data depends on the initial elastic recovery of the sample. The plastic indentation depth is estimated from an intercept between the zero force axis and a straight line drawn at a tangent to the initial part of the unloading slope.

Similar hardness measurements were also done using a desktop Instron Universal Testing Machine (Model 5566) fitted with a 10 N load cell, and the data analysis performed in the same way.

iii) Deposition and whiteness of deposit

Another test of the properties of a composition is the amount of the composition which is delivered onto a surface when the composition is drawn across that surface (representing the application of a stick product to human skin). To carry out this test of deposition, a sample of the composition with standardized shape and size is fitted to apparatus which draws the sample across a test surface under standardized conditions. The amount transferred to the surface is determined as an increase in the weight of the substrate to which it is applied. If desired the colour, opacity or clarity of the deposit may subsequently be determined.

A specific procedure for such tests used apparatus to apply a deposit from a stick onto a substrate under standardized conditions and then measures the mean level of white deposits using image analysis.

The substrates used were a: 12×28 cm strip of grey abrasive paper (3M™ P800 WetorDry™ Carborundum paper)

b: 12×28 cm strip of black Worsted wool fabric.

The substrates were weighed before use. The sticks were previously unused and with domed top surface unaltered.

The apparatus comprised a flat base to which a flat substrate was attached by a clip at each end. A pillar having a mounting to receive a standard size stick barrel was mounted on an arm that was moveable horizontally across the substrate by means of a pneumatic piston.

Each stick was kept at ambient laboratory temperature overnight before the measurement was made. The stick was advanced to project a measured amount from the barrel. The barrel was then placed in the apparatus and a spring was positioned to biassed the stick against the substrate with a standardised force. The apparatus was operated to pass the stick laterally across the substrate eight times. The substrate was carefully removed from the rig and reweighed.

Whiteness of Deposit

The deposits from the previous test were assessed for their whiteness after an interval of 24 hours approximately.

This was done using a Sony XC77 monochrome video camera with a Cosmicar 16 mm focal length lens positioned vertically above a black table illuminated from a high angle using fluorescent tubes to remove shadowing. The apparatus was initially calibrated using a reference grey card, after the fluorescent tubes had been turned on for long enough to give a steady light output. A cloth or Carborundum paper with a deposit thereon from the previous test was placed on the table and the camera was used to capture an image. An area of the image of the deposit was selected and analysed using a Kontron IBAS image analyser. This notionally divided the image into a large array of pixels and measured the grey level of each pixel on a scale of 0 (black) to 255 (white). The average of the grey intensity was calculated. This was a measure of the whiteness of the deposit, with higher numbers indicating a whiter deposit. It was assumed that low numbers show a clear deposit allowing the substrate colour to be seen.

It has been found desirable to carry out deposition of a standard stick composition, and determine the whiteness of the deposit, as a control.

iv) Light transmission

The translucency of a composition may be measured by placing a sample of standardised thickness in the light path of a spectrophotometer and measuring transmittance, as a percentage of light transmitted in the absence of the gel.

We have carried out this test using a dual-beam spectrophotometer. The sample of composition was poured hot into a 4.5 ml cuvette made of polymethylmethacrylate (PMMA) and allowed to cool to an ambient temperature of 20–25° C. Such a cuvette gives a 1 cm thickness of composition. Measurement was carried out at 580 nm, with an identical but empty cuvette in the reference beam of the spectrophotometer, after the sample in the cuvette had been held for 24 hours. We have observed that a composition which gives a transmittance of as little as 1% in this test is perceived by eye as "translucent". If a stick is made from a composition with 3% transmittance, it is possible to see cavities made by boring beneath the surface of the sample. By contrast, a conventional stick structure with stearyl alcohol is so opaque that it is impossible to see beneath its surface. A transmittance measured at any temperature in the range from 20–25° C. is usually adequately accurate, but measurement is made at 22° C. if more precision is required. In a number of preferred examples we have achieved a transmittance of 20% or above.

Preparation

Compositions of this invention can be produced by processes which involve forming a heated mixture of the composition at a temperature such that the structurant is in solution in the continuous phase, pouring that mixture into a mould, which may take the form of a dispensing container, and then cooling the mixture whereupon the structurant solidifies within water-immiscible liquid phase, and thereby gels that phase and hence the whole composition.

A convenient process sequence comprises first forming a solution of the structurant in the water-immiscible liquid. This is normally carried out by agitating the mixture at a temperature sufficiently high that all the structurant dissolves (the dissolution temperature) such as a temperature in a range from 50 to 120° C.

If any emulsifier is being used, this is conveniently mixed into this liquid phase. Separately an aqueous or hydrophilic disperse phase is prepared by introduction of antiperspirant active into the liquid part of that phase (if this is necessary; antiperspirant actives can sometime be supplied in aqueous solution which can be utilised as is). This solution of antiperspirant active which will become the disperse phase is preferably heated to a temperature similar to that of the continuous phase with structurant therein, but without exceeding the boiling point of the solution and then mixed with the continuous phase. Alternatively the solution is introduced at a rate which maintains the temperature of the mixture. If necessary a pressurised apparatus could be used to allow a higher temperature to be reached. After the two phases are mixed, the resulting mixture is introduced into a dispensing container such as a stick barrel. This is usually carried out at a temperature 5 to 30° C. above the setting temperature of the composition. The container and contents are then cooled to ambient temperature. Cooling may be brought about by nothing more than allowing the container and contents to cool. Cooling may be assisted by blowing ambient or even refrigerated air over the containers and their contents.

EXAMPLES

The examples below were prepared using a number of materials set out with their proprietary names in the following list. All temperature are in degrees Celsius. Refractive indices were measured at 22° C.

1 & 2) Volatile cyclic silicones (cyclomethicones) DC 245 and DC 345 (Dow Corning)
3 & 4) Non-volatile silicone fluids DC 556 and DC 710 (Dow Corning)
5) Polydecene (Silkflo 364NF from Albemarle)
6) Isostearyl Alcohol (abbreviated to ISA-Prisorine 3515 from Unichema)
7) C12–15 alkyl benzoate (Finsolv TN from Fintex)
8) Mineral Oil (Sirius M70 from Dalton)
9) Polypropyleneglycol 14 butylether (Fluid AP from Amercol)
10) Isopropyl myristate (abbreviated to IPM from Unichema)
11) Isohexadecane (Permethyl 101A from Presperse Inc)
12) Isoeicosane (Permethyl 102A from Presperse Inc)
13) Cetyl dimethicone copolyol (Abil EM90 emulsifier from Th. Goldschmidt)
14) N-lauryl-L-glutamic acid di-n-butylamide (GP1 from Ajinomoto)
15) 50% aqueous solution of Al/Zr pentachlorohydrate (Zirkonal 50 from Giulini)
16) Al/Zr Tetrachlorohydrex glycine complex 30% in propylene glycol (WA2Z 8106 from Westwood)
17) Al/Zr tetrachlorohydrex glycine complex (AZG 375 from Summit)
18) Glycerol (from Aldrich)
19) Propylene glycol (from Fisons)
20) Bis-phenylpropyldimethicone, a non-volatile silicone fluid (SF 1555 from G E Silicones)
21) 1-octyldodecanol (Eutanol G from Henkel/Cognis)
22) Hydrogenated polyisobutene (Panalene-L-14E from Amoco)
23) Hydrogenated polyisobutene (Fancol 800 from Fanning Corporation)
24) Polyglyceryl-3-diisostearate (Lameform TGI from Henkel/Cognis)
25) Polyglyceryl-2-dipolyhydroxystearate (Dehymuls PGPH from Henkel/Cognis)
26) Polyalpha Olefins (Puresyn 4 from Mobil Chemical)

Example 1

Emulsion sticks were prepared with formulations as set out in the table below.

To prepare these sticks, the cyclomethicone was mixed with the other organic liquids including the cetyl dimethicone copolyol which functioned as an emulsifier (silicone surfactant) and with the GP1 structurant. The mixture was heated with gentle stirring to a temperature of 120° C. to dissolve the structurant. It was then allowed to cool to 100° C.

The disperse phase (also referred to as internal phase) was an aluminium zirconium active dissolved in a polyol and water. This disperse phase was pre-heated to 92° C. and added slowly to the organic liquids over a period of one minute while mixing with a Silverson mixer. After addition was complete the formulation was mixed at higher speed for five minutes. Stirring speed was then reduced for a further one minute after which the mixture was poured into stick barrels and allowed to cool undisturbed to room temperature. The sticks were tested by penetrometer, in one case by texture analyser, and for whiteness of deposits by the test procedures given earlier. It was observed that the sticks were translucent.

| Examples | 1.1 | 1.2 | 1.3 | 1.4 |
|---|---|---|---|---|
| | Parts by weight | | | |
| Cyclomethicone DC 245 (1) | 18 | 22.25 | 21.7 | — |
| Cyclomethicone DC 345 (2) | — | — | — | 23.7 |
| Polydecene (5) | 22.75 | 27.5 | 27.4 | — |
| Finsolv TN (7) | 13.3 | 13.3 | 13.3 | 12.6 |
| Isostearyl alcohol (6) | 12 | 12 | 12 | 11.5 |
| GP1 (14) | 4 | 4 | 4 | 3.8 |
| Cetyl Dimethicone Copolyol (13) | 1 | 1 | 1 | 0.95 |
| Zirkonal 50 (15) | 40 | 40 | 40 | 40 |
| Glycerol (18) | — | — | — | 10 |
| | Properties | | | |
| penetration depth (mm) | 18.7 | 21.6 | 17.0 | 17.5 |
| Hardness by texture analyser (N/mm$^2$) | — | — | — | 0.067 |
| Whiteness on grey paper 24 hours after deposition | 26 | — | — | 32 |
| Whiteness on black wool 24 hours after deposition | | | | 19 |

Example 2

Cellobiose was esterified with nonanoic acid to yield the fully esterified product in the form of its α-anomer following a procedure generally as described in Takada et al, Liquid Crystals, Volume 19, page 441 (1995).

The following materials were used:

β-D-cellobiose, 20 grams, 0.058 moles

Nonanoic acid, 591.6 grams, 3.74 moles

Trifluoroacetic anhydride, 297.6 grams, 1.42 moles.

These materials were obtained from Acros Organics-Fisher Scientific.

Into a 2 liter flange pot equipped with an overhead stirrer, water condenser and addition inlet was placed the nonanoic acid together with the trifluoroacetic anhydride. The resultant clear mixture was stirred up and heated to 100° C. using a silicone oil bath and temperature probe. During heating it was noted that the colour of the reaction mixture darkened and developed a dark brown tinge. After allowing the mixture to stir for one hour at 100° C., the cellobiose was slowly added via a solid powder funnel to the dark activated solution, and a dirty brown suspension was formed which re-dissolved forming a clear black solution within 10–20 minutes.

The reaction flask was then maintained at 100° C. for a total of 6 hours then cooled down to ambient laboratory temperature. Next the contents of the flask were transferred into 2 liters of methanol containing 10% de-ionised water in an ice-cooled 5 liter beaker. Immediately an off-white solid precipitate came out of solution, this was filtered off and collected. The crude solid was recrystallised a total of 4 times from a tetrahydrofuran/methanol solution producing a white solid product.

The product cellobiose octa-nonanoate also designated esterified cellobiose—$C_9$ was obtained in a quantity of 31.5 g which was a 37% yield. It had a melting point of 110° C. The infra-red spectrum showed an absorption peak at 1739 $cm^{-1}$ for the ester carbonyl group. The amount of free acid could be determined from its absorption peak at 1705 $cm^{-1}$.

The n.m.r. spectrum showed the amount of cellobiose which was fully esterified to be 93.5% and showed the proportions of product which were the α- and β-anomers, (93.5% α-anomer).

This procedural route was also used to prepare the corresponding esters of cellobiose with other carboxylic acids, including decanoic and undecanoic acids.

A number of emulsion sticks were prepared using esterified cellobiose as structurant in formulations set out in the following tables. The continuous and disperse phases were formulated to have refractive indices which matched closely at the value given in the tables.

To prepare these sticks, the cyclomethicone was mixed with the other organic liquids (if any) including the cetyl dimethicone copolyol which functioned as an emulsifier (silicone surfactant) and the mixture was heated with gentle stirring to a temperature 5 to 10° C. above a temperature at which the structurant had been found to dissolve in a previous trial. The esterified cellobiose structurant was then added and allowed to dissolve.

The disperse phase (also referred to as internal phase) was an aluminium zirconium active dissolved in water or in a mixture of a polyol and water. This disperse phase was pre-heated to the same temperature as the organic oils containing the esterified cellobiose and added slowly to them over a period of one minute while mixing with a Silverson mixer. After addition was complete the formulation was mixed at higher speed for five minutes. Stirring speed was then reduced for a further one minute after which the mixture was poured into stick barrels and allowed to cool undisturbed to ambient laboratory temperature. The sticks were tested by penetrometer, by texture analyser, for whiteness of deposits and for light transmittance in each instance by the test procedures given earlier.

| Examples | 2.1 | 2.2 | 2.3 | 2.4 | 2.5 | 2.6 |
|---|---|---|---|---|---|---|
| | % by weight | | | | | |
| Cyclomethicone DC245 (1) | 22.625 | 18.75 | 25.5 | 19 | 26 | 17.75 |
| Mineral Oil (8) | 22.625 | — | — | — | — | — |
| Polydecene (5) | — | 22.5 | 15.75 | 22 | 15 | 22 |
| PPG-14 Butyl Ether (9) | — | 4 | 4 | — | — | 4.25 |
| Isostearyl Alcohol (6) | — | — | — | 4.25 | 4.25 | — |
| Cellobiose octa-nonanoate | 3.75 | 3.75 | 3.75 | 3.75 | 3.75 | 5 |
| Cetyl Dimethicone Copolyol (13) | 1 | 1 | 1 | 1 | 1 | 1 |
| Zirkonal 50 (15) | 40 | 40 | 40 | 40 | 40 | 40 |
| Glycerol (18) | 10 | 10 | 7.5 | 10 | 7.5 | 10 |
| Water | — | — | 2.5 | — | 2.5 | — |
| | Properties | | | | | |
| Matched Refractive index of phases | 1.43 | 1.43 | 1.425 | 1.435 | 1.425 | 1.43 |
| penetration depth (mm) | 19.3 | 18.5 | 17.3 | 24.7 | 23.6 | 12.4 |
| Hardness by texture analyser (N/mm$^2$) | 0.11 | 0.12 | 0.08 | 0.07 | 0.06 | 0.17 |
| Whiteness on grey paper 24 hours after deposition | — | 15 | 16 | 18 | 19 | 16 |
| Whiteness on black wool 24 hours after deposition | — | 24 | 28 | 25 | 30 | 26 |
| Transmittance at 580 nm | — | 38% | 33% | 41% | 35% | 51% |

| Examples | 2.7 | 2.8 | 2.9 | 2.10 | 2.11 | 2.12 |
|---|---|---|---|---|---|---|
| | % by weight | | | | | |
| Cyclomethicone DC245 (1) | 16.75 | 18 | 14.02 | 28.4 | 4.5 | — |
| Cyclomethicone DC345 (2) | — | — | — | — | — | 4.4 |
| Mineral Oil (8) | — | — | — | — | — | 43.4 |
| Polydecene (5) | 20.75 | 22.75 | 17.72 | 13.1 | 50.75 | — |
| PPG-14 Butyl Ether (9) | 4 | 4.5 | 3.51 | 3.75 | — | — |
| Cellobiose octa-nonanoate | 7.5 | 3.75 | 3.75 | 3.75 | 3.75 | — |
| Cellobiose octa-decanoate | — | — | — | — | — | 2.4 |
| Cetyl Dimethicone Copolyol (13) | 1 | 1 | 1 | 1 | 1 | 1 |
| Zirkonal 50 (15) | 40 | — | 40 | 40 | — | — |
| Westwood Active (16) | — | — | — | — | — | 48.8 |
| Glycerol (18) | 10 | 4 | 17.5 | 6.25 | 12 | — |
| Water | — | 14 | 2.5 | 3.75 | 8 | — |
| Propylene glycol (19) | — | 12 | — | — | — | — |
| AZG375 (17) | — | 20 | — | — | 20 | — |
| | Properties | | | | | |
| Matched Refractive index of phases | 1.43 | 1.43 | 1.43 | 1.42 | 1.45 | 1.46 |
| penetration depth (mm) | 11 | 14.5 | 14.9 | 15.1 | 14.8 | — |
| Hardness by texture analyser (N/mm$^2$) | 0.29 | 0.11 | 0.14 | 0.13 | 0.11 | — |
| Whiteness on grey paper 24 hours after deposition | 17 | 20 | 18 | 21 | 16 | — |
| Whiteness on black wool 24 hours after deposition | 25 | 28 | 25 | 31 | 19 | — |
| Transmittance at 580 nm | 48% | 82% | 65% | 30% | 72% | 74% |

| Examples | 2.13 | 2.14 | 2.15 | 2.16 | 2.17 |
|---|---|---|---|---|---|
| | % by weight | | | | |
| Cyclomethicone DC245 (1) | 41.85 | 35.4 | 10.04 | 10.64 | 6.96 |
| Permethyl 101A (11) | 2.15 | — | — | — | — |
| Permethyl 102A (12) | — | 8.6 | — | — | — |
| Polydecene (5) | — | — | 12.7 | 13.45 | 8.8 |
| PPG-14 Butyl Ether (9) | — | — | 2.51 | 2.66 | 1.74 |
| Isostearyl Alcohol (6) | — | — | — | — | — |
| Esterified Cellobiose $C_9$ | 5 | 5 | 3.75 | 2.25 | 1.5 |
| Cetyl Dimethicone Copolyol (13) | 1 | 1 | 1 | 1 | 1 |
| Zirkonal 50 (15) | 40 | 40 | 52.71 | 52.71 | 60.24 |
| Glycerol (18) | 0.75 | 4.5 | 17.29 | 17.29 | 19.76 |
| Water | 9.25 | 5.5 | — | — | — |
| | Properties | | | | |
| Matched Refractive index of phases | 1.40 | 1.41 | 1.43 | 1.43 | |
| penetration depth (mm) | 13.5 | 13.2 | 12.0 | 16.8 | |
| Hardness by texture analyser (N/mm$^2$) | 0.16 | 0.15 | 0.13 | 0.07 | |
| Whiteness on grey paper 24 hours after deposition | 59 | 61 | 24 | 24 | |
| Whiteness on black wool 24 hours after deposition | 122 | 24 | 15 | 16 | |
| Transmittance at 580 nm | 2.7% | 5% | 33% | 73% | |

Example 3

Sticks were prepared in accordance with the procedure given in Example 2. The sticks were tested for hardness by texture analyser and/or by penetrometer. They were observed to give deposits of low whiteness, but numerical data were not recorded. Compositions and some properties are given in the tablet below.

The refractive indices of the water-immiscible continuous phase and the polar antiperspirant active solution were matched sufficiently to give translucent sticks. Values of transmittance are included in the table.

| Examples | 3.1 | 3.2 | 3.3 | 3.4 | 3.5 |
|---|---|---|---|---|---|
| | % by weight | | | | |
| Cyclomethicone DC 245 (1) | 7.6 | 6.8 | 36.5 | 1.7 | 1.25 |
| isostearyl alcohol (6) | — | — | — | 23.3 | — |
| octyldodecanol (21) | — | — | — | — | 23.1 |
| SF1555 (20) | 37.43 | 37.7 | 7 | — | — |
| Silkflo 364 (5) | — | — | — | 16.8 | 17.65 |
| Esterified Cellobiose-C10 | 8.12 | 7.3 | 7.8 | 7 | 7 |
| Cetyl Dimethicone Copolyol (Abil EM90) (13) | 1.1 | 1 | 1 | 1 | 1 |
| Westwood active (16) | 43.54 | 41 | 42 | 40 | 40 |
| Glycerol (18) | — | 4.7 | 5.2 | 6.8 | 6.5 |
| Water | 2.21 | 1.5 | 0.5 | 3.4 | 3.5 |
| Properties | | | | | |
| Matched RI of phases | 1.45 | 1.45 | 1.46 | 1.45 | 1.45 |
| penetration depth (mm) | 9.1 | 6.9 | 8.7 | 8.8 | 9.1 |
| Hardness by texture analyser (N/mm$^2$) | 0.37 | 0.03 | 0.08 | 0.04 | 0.19 |
| Transmittance at 580 nm (%) | 8 | 3 | 5 | 6 | 5 |

Example 4

The procedure used in Example 2 was repeated to prepare a number of emulsion sticks with formulations set out in the following tables. As in Example 2, the continuous and disperse phases were formulated to have refractive indices which matched closely at the value given in the tables. The sticks were tested for hardness by texture analyser and/or by penetrometer. They were observed to give deposits of low whiteness, consistent with their good clarity, but numerical data were not recorded.

The refractive indices of sample quantities of the water-immiscible liquid mixture and the antiperspirant active solutions were checked before making the sticks. If necessary their formulations were modified very slightly to optimise the refractive index match.

| Examples | 4.1 | 4.2 | 4.3 | 4.4 | 4.5 | 4.6 |
|---|---|---|---|---|---|---|
| | % by weight | | | | | |
| Permethyl 102A (12) | 41.36 | — | — | — | — | — |
| Panalene L-14E (22) | — | — | 22 | — | — | — |
| Fancol 800 (23) | — | — | — | 22 | 22 | — |
| Puresyn 4 (26) | — | — | — | — | — | 22 |
| DC245 (1) | 2.64 | 11.4 | 22 | 22 | 22 | 22 |
| SF1555 (20) | — | 34.1 | — | — | — | — |
| Esterified cellobiose C9 | 5 | 4.9 | 5 | 5 | 5 | 5 |
| Abil EM90 (13) | 1 | 1 | 1 | 1 | 1 | 1 |
| Zirkonal 50 (15) | — | — | 40 | 40 | 36.6 | 40 |
| Westwood active (16) | 50 | 48.6 | — | — | — | — |
| Glycerol (18) | — | — | 9.35 | 7.5 | 13.4 | 8.75 |
| Water | — | — | 0.65 | 2.5 | — | 1.25 |
| Properties | | | | | | |
| Matched RI of phases (at 25° C.) | 1.46 | 1.45 | 1.431 | 1.425 | 1.437 | 1.429 |
| penetration depth (mm) | 9 | 11 | 10.5 | 12.1 | 7.9 | 8.8 |
| Hardness by texture analyser (N/mm$^2$) | 0.11 | 0.11 | 0.13 | 0.12 | 0.11 | 0.10 |
| Transmittance at 580 nm (%) | 68 | 70 | 40 | 6 | 70 | 37 |

| Examples | 4.7 | 4.8 | 4.9 | 4.10 | 4.11 |
|---|---|---|---|---|---|
| | % by weight | | | | |
| DC245 (1) | 22 | 22.25 | 22.25 | 21.625 | — |
| DC556 (3) | 22 | — | — | — | — |
| Silkflo364 (5) | — | — | — | — | 44 |
| Permethyl 102A (12) | — | 22.25 | — | — | — |
| Panalene-L-14E (22) | — | — | — | 21.625 | — |
| SF1555 (20) | — | — | 22.25 | — | — |
| Abil EM90 (13) | 1 | 0.5 | 0.5 | — | 1 |
| Lameform TGI (24) | — | — | — | 0.875 | — |
| Dehymuls PGPH (25) | — | — | — | 0.875 | — |
| Esterified cellobiose C9 | 5 | 5 | 5 | 5 | 5 |
| Zirkonal 50 (15) | 40 | 40 | 40 | 40 | 50 |
| Glycerol (18) | 9 | 8 | 9 | 9.8 | — |
| Water | 1 | 2 | 1 | 0.2 | — |
| Properties | | | | | |
| Matched RI of phases (at 25° C.) | 1.428 | 1.43 | 1.43 | 1.43 | 1.46 |
| penetration depth (mm) | 9.0 | 11 | 11 | 10.5 | 9 |
| Hardness by texture analyser (N/mm$^2$) | 0.10 | 0.09 | 0.16 | 0.13 | 0.13 |
| Transmittance at 580 nm (%) | 40 | 22 | 33 | 36 | 24 |

| Examples | 4.12 | 4.13 | 4.14 | 4.15 | 4.16 | 4.17 |
|---|---|---|---|---|---|---|
| | % by weight | | | | | |
| DC245 (1) | — | — | — | 22 | 22 | 18 |
| Silkflo364 (5) | 44 | — | — | — | — | 5.3 |
| Permethyl 102A (12) | — | 44 | — | 22 | — | — |
| Panalene-L-14E (22) | — | — | 44 | — | — | — |
| SF1555 (20) | — | — | — | — | 22 | — |
| Octyldodecanol (21) | — | — | — | — | — | 21.9 |
| Abil EM90 (13) | 1 | 1 | 1 | 1 | 1 | 1 |
| Esterified Cellobiose C9 | 5 | 5 | 5 | 5 | 5 | 5 |
| Zirkonal 50 (15) | 18 | 21.5 | 12 | — | — | 37.8 |
| AZG-375 (17) | — | — | — | 25 | 25 | — |
| Glycerol (18) | 32 | 28.5 | 38 | 0.6 | 2.5 | 11 |
| Water | — | — | — | 24.4 | 22.5 | — |
| Properties | | | | | | |
| Matched refractive index of phases (at 25° C.) | 1.45 | 1.45 | 1.46 | 1.43 | 1.43 | 1.43 |
| penetration depth (mm) | 9 | 9 | 7 | 9 | 8 | — |
| Hardness by texture analyser (N/mm$^2$) | 0.13 | 0.15 | 0.20 | — | 0.21 | 0.12 |
| Transmittance at 580 nm (%) | 74 | 46 | 82 | 53 | 41 | 24 |

What is claimed is:

1. An antiperspirant composition which is a structured emulsion comprising
   i) a continuous phase containing water-immiscible liquid carrier and a structurant,
   ii) a disperse phase which is a solution of antiperspirant active in water, optionally including water-soluble solvent, where the composition has at least 1% light transmittance at 580 nm through a 1 cm thickness of the composition at 22° C.

2. A composition according to claim 1 wherein the continuous phase with structurant therein is a gel which is able to melt to become mobile on heating.

3. A composition according to claim 1 wherein the structurant forms a network of fibres extending throughout the water-immiscible continuous phase.

4. A composition according to claim 1 wherein the continuous phase contains liquid silicone in an amount which is at least 10% by weight of the whole composition.

5. A composition according to claim 1 wherein the continuous phase contains hydrocarbon oil in an amount which is at least 10% by weight of the liquid carrier.

6. A composition according to claim 1 wherein the continuous phase does not contain more than 10% of its own weight, better not more than 5%, of any constituent which is a water-miscible compound.

7. A composition according to claim 1 wherein the continuous phase is from 15 to 95% of the weight of the composition and the disperse phase is from 5 to 85% of the weight of the composition.

8. A composition according to claim 1 wherein the continuous phase is from 15% to 60% of the weight of the composition and the disperse phase is from 40 to 85% of the weight of the composition.

9. A composition according to claim 1 wherein the total amount of structurant is from 0.5 to 20% by weight of the continuous phase.

10. A composition according to claim 1 wherein the total amount of structurant is from 0.5 to 12% by weight of the whole composition.

11. A composition according to claim 1 wherein the disperse phase contains a diol or polyol with a solubility in water of at least 10% by weight at 22° C.

12. A composition according to claim 1 wherein the composition contains an antiperspirant active selected from the group of antiperspirant compounds of aluminium, zirconium and mixtures thereof in an amount from 5 to 35% by weight of the composition.

13. A composition according to claim 11 characterised in that the antiperspirant active comprises an aluminium and/or zirconium halohydrate, an activated aluminium and/or zirconium halohydrate, or an aluminium and/or zirconium complex or an activated aluminium and/or zirconium complex.

14. A composition according to claim 13 which is a halohydrate or complex in which aluminium and zirconium are both present.

15. A composition according to claim 1 which contains from 0.1% to 10% by weight of a nonionic emulsifier.

16. A composition according to claim 1 which is a firm gel such that a penetrometer needle with a cone angle of 9 degrees 10 minutes, drops into the gel for no more than 30 mm when allowed to drop under a total weight of 50 grams for 5 seconds.

17. A composition according to claim 1 which has at least 3% light transmittance at 580 nm through a 1 cm thickness of the composition at 22° C.

18. A composition according to claim 15 which has at least 20% light transmittance at 580 nm through a 1 cm thickness of the composition at 22° C.

19. A composition according to claim 1 wherein the refractive indices of the continuous phase and disperse phase differ by no more than 0.003 and both have a value within a range from 1.41 to 1.46.

20. A composition according to claim 19 wherein the refractive indices of the continuous and disperse phases are not over 0.07 below and not over 0.04 above the refractive index of the structurant.

21. A composition according to claim 1 accommodated within a dispensing container.

22. An antiperspirant product comprising a composition according to claim 1 and a dispensing container with the composition therein, said container having at least one aperture for delivery of the contents of the container, and means for urging the contents of the container to the said aperture or apertures.

23. A product according to claim 22 wherein the composition is in the form of a stick and the container has an open end at which an end portion of the stick of composition is exposed for use.

24. A process for the production of an antiperspirant composition as defined in claim 1 comprising, concurrently or in any order, the steps of
   incorporating a structurant into a water-immiscible liquid carrier
   mixing the liquid carrier with a disperse liquid phase which is a solution of an antiperspirant active in water, optionally including a water-soluble solvent,
   heating to an elevated temperature at which the structurant is soluble in the water-immiscible liquid carrier, followed by
   introducing the mixture into a mould which preferably is a dispensing container, and then
   cooling or permitting the mixture to cool to a temperature at which it is thickened or solidified.

25. A method for preventing or reducing perspiration on human skin comprising topically applying to the skin a composition according to claim 1.

* * * * *